(12) United States Patent
Mabary et al.

(10) Patent No.: US 7,236,820 B2
(45) Date of Patent: Jun. 26, 2007

(54) STANDARDIZED SWALLOW CHALLENGE MEDIUM AND METHOD OF USE FOR ESOPHAGEAL FUNCTION TESTING

(75) Inventors: Jerry E. Mabary, Littleton, CO (US); Ian N. Askill, Colorado Springs, CO (US)

(73) Assignee: Sandhill Scientific, Inc., Highlands Ranch, CO (US)

( * ) Notice: Subject to any disclaimer, the term of this patent is extended or adjusted under 35 U.S.C. 154(b) by 465 days.

(21) Appl. No.: 10/768,956

(22) Filed: Jan. 29, 2004

(65) Prior Publication Data

US 2004/0254495 A1    Dec. 16, 2004

Related U.S. Application Data

(60) Provisional application No. 60/443,356, filed on Jan. 29, 2003.

(51) Int. Cl.
*A61B 5/00* (2006.01)
(52) U.S. Cl. .................... 600/547; 600/593
(58) Field of Classification Search ............. 600/547, 600/593, 350
See application file for complete search history.

(56) References Cited

U.S. PATENT DOCUMENTS 6,461,589 B2 * 10/2002 Robbins ............... 424/9.41

2003/0044351 A1 * 3/2003 Robbins ............... 424/9.1

OTHER PUBLICATIONS

Nyugen, N.G., et al.; Am J Gastroenterol 2006;101:2476-2484.*
Frieling et al., "Comparision between intraluminal multiple electric impedance measurement and manometry in the human oesophagus", Neurogastroenterol Mot. (1996) 8, pp. 45-50.
Nguyen et al., "Dynamics of esophageal bolus transport in healthy subjects studied using multiple intraluminal impedancometry", American Physiological Society (1997), pp. 958-964.
Jiri Silny, "Intraluminal Multiple Electric Impedance Procedure for Measurement of Gastrointestinal Motility", Journal of Gastrointestinal Motility (1991), pp. 151-162.
Fass et al., "Measuring Esophageal Motility with a New Intraluminal Impedance Device", Scand Journal of Gastroenterology (1994), pp. 693-702.

* cited by examiner

*Primary Examiner*—Charles A. Marmor, II
*Assistant Examiner*—Karen E Toth
(74) *Attorney, Agent, or Firm*—Cochran Freund & Young LLC; James R. Young

(57) ABSTRACT

A swallow challenge medium (10) is thixotropic for easy swallowing and to provide enough viscosity for effective challenge to peristalsis (20) and has high ionic density for effective impedance measurements by contact with electrodes (41–48) positioned in a person's esophagus (E) or oropharynx during swallow testing. The medium (10) also has a high surface tension so as not to adhere to or coat the electrodes (41–48) or probe (12) surfaces. These physical characteristics are stabilized and consistent enough to provide standard for esophageal and/or oropharyngeal function testing and diagnostics.

7 Claims, 8 Drawing Sheets

STANDARDIZED SWALLOW CHALLENGE MEDIUM AND METHOD OF USE FOR ESOPHAGEAL FUNCTION TESTING

CROSS REFERENCE TO RELATED APPLICATION

The present application claims priority of U.S. Provisional Application No. 60/443,356, filed Jan. 29, 2003, which application is incorporated herein by reference.

FIELD OF THE INVENTION

The invention relates generally to assessing esophageal condition. More particularly, the invention relates to an apparatus and method for measuring the movement of a bolus in the esophagus after swallowing with a swallow challenge medium useful for such measurements.

BACKGROUND OF THE INVENTION

Accurate measurements of physiological parameters of the esophagus under realistic swallowing conditions are valuable in diagnosing esophageal diseases such as gastroesophageal reflux disease (GERD), abnormal functioning of the lower esophageal sphincter (LES) and peristaltic muscular contractions and movements in the esophagus, and the like. When a person with a healthy esophagus swallows, circular muscles in the esophagus contract. The contractions begin at the upper end of the esophagus and propagate downwardly toward the lower esophageal sphincter ("LES"). These muscular contractions are commonly called peristaltic movements, contractions, or waves, or simply as "peristalsis". The function of the peristaltic muscle contractions, i.e., to propel food and drinks through the esophagus to the stomach, is sometimes called the motility function, but is also often used to refer to peristalsis. Therefore, the terms "motility" or "motility function" and "peristalsis" are sometimes used interchangeably.

The LES is normally closed, but it opens momentarily, when a peristaltic contraction approaches it, to admit the bolus of food or drink into the stomach. As a peristaltic contraction passes through each point along the esophagus, the esophageal pressure at that point rises to a maximum and then falls back to a base pressure at the relaxed state. This peristaltic propagation of the esophageal contraction tends to propel any swallowed volume of mass, which is called a "bolus", ahead of the point of peak pressure and down the esophagus toward the stomach. The motility function of the esophagus, i.e., the esophagus' ability to move a mass, is dependent on several factors, including the peristaltic pressure profile and the characteristics of the esophageal muscles.

Esophageal pressure measurement, or manometry, as well as electrical impedance have been used to assess motility function of the esophagus and bolus transit dynamics in the esophagus. A typical esophageal manometer includes an elongated catheter or probe with pressure sensors located along its length. The catheter or probe is designed to be inserted into the esophagus, typically reaching the LES and extending into the stomach, of a patient, with the pressure sensors positioned at the LES and at a plurality of other specific points along the length of the esophagus at predetermined distances above the LES. During a typical test, the patient swallows a specific amount of water with the manometer placed in the esophagus. The esophageal pressure at the pressure sensors can be measured and used as an indication of the magnitude and sequence of the peristaltic contractions. In addition, because the positions of the sensors are known, the velocity of the peristaltic motion can also be ascertained from the location of the peak pressure as a function of time. The test can be repeated a number of times to obtain a set of pressure and velocity values, a statistical analysis of which may be used for diagnostic purposes. For example, according to one protocol, ten 5-ml water swallows are to be performed at approximately 30-second intervals. The patient's functional response is determined as a percentage of the swallows. For example, a result of such test swallows may show that 80% of the swallows were followed by a contraction pressure of 30 mmHg or greater with an onset velocity of about 8 cm/sec, and, therefore, showed normal peristalsis; the remaining 20% of the swallows resulted in a contraction pressure of less than 30 mmHg and, therefore, are deemed to be ineffective peristalsis.

While the conventional manometry (pressure measurements) is useful for assessing certain aspects of the physiology of the esophagus, i.e., peristaltic muscular activity in the esophagus and LES are detectable as pressure changes, the technique has its limitations in at least two respects. Esophageal manometry does not measure or predict bolus transit, which is the actual movement of a mass of swallowed material through the esophagus. Esophageal peristalsis generally is triggered by a swallowing action and proceeds whether or not any substance is actually swallowed, and the peristaltic muscular contractions may proceed regardless of whether the bolus is actually moving through the esophagus. Further, some swallowed material, such as water, will flow by gravity through the esophagus, even if there are no peristaltic muscular contractions or if they are irregular or erratic. Thus, the mere manometric detection of propagating peristaltic muscular contractions, even if they are properly timed and of normal amplitude (strength), does not necessarily mean that any bolus is being propelled by the peristalsis. Thus, incomplete bolus transit may not be detected by manometry alone. Other substances could be swallowed, such as food, but resulting data, such as impedance, would vary, depending on the characteristics of the food or other substances.

Electrical impedance at a plurality of points in the esophagus can be used to detect and monitor movement of a bolus through the esophagus. Essentially, a bolus of water or food will have different electrical impedance than the non-filled esophagus, so a change in impedance in the esophagus indicates presence of a bolus. Therefore, an elongated probe positioned in the esophagus with a plurality of impedance and/or acidity sensors dispersed along its length can be used to detect and monitor the bolus transit, i.e., the movement of a bolus through the esophagus. Therefore, by combining manometry (pressure measurements) with simultaneous impedance measurements, both peristalsis and bolus transit can be quantified, and these measurements, if accurate and dependable, can be combined to determine whether the bolus movement and the peristaltic contractions are in proper synchronization or if there is an abnormal or dysfunctional relationship between them.

Unfortunately, prior to this invention, it was very difficult, if not impossible, to get consistent, accurate, reliable, and repeatable impedance measurements, even if the impedance probes, sensors, and measuring equipment, itself, was well-designed and in good working condition. The problem was that the swallow media available for such tests were inadequate. For example, water as a medium for swallow tests provides very little resistance to peristaltic propulsion and is often inadequate to cause esophageal abnormalities to manifest themselves during the test. Water also has inconsistent ionic content, varying from one source to another or from one municipal water system to another, which causes variations in impedance measurements and is often insufficient to even make meaningful impedance measurements. Saline solution has more ionic content, but it provides insufficient resistance to peristaltic propulsion to cause esophageal abnormalities to be detected. Water and saline solution also do not remain in a distinct, well-defined bolus mass and, instead, run and spread by gravity through the length of the esophagus, bridging many or all of the impedance sensor electrodes so that sensing distinct bolus transit dynamics in relation to manometric detection of peristalsis is difficult, if not impossible. Other substances, such as yogurt, mash potatoes, or other foods could be swallowed, but resulting data, such as impedance, would vary, depending on the physical characteristics of the foods, such as ionic content, viscosity, surface tension, and the like. Also, foods tend to coat or stick to the probe and impedance sensor electrodes on the probe, even after the bolus has passed, which interferes with subsequent impedance measurements and makes it difficult and often impossible to detect bolus transit in subsequent swallows. These and other deficiencies contribute to erratic, inconsistent, unreliable, and unrepeatable test results.

A state-of-the-art technique for observing and assessing actual bolus transit includes a barium esophagram diagnostic test, in which a patient in front of an X-ray camera performs swallows of a contrast medium that shows distinctly in an X-ray image. This diagnostic method, however, has a number of drawbacks as well, including the high cost of equipment and exposure of patients to ionizing radiation, and it is not conducive to ambulatory testing. In addition, manometric data synchronized with bolus transit are not available from barium esophagram tests. Such synchronized data is often important in assessing the complex physiology of bolus transit dynamics.

SUMMARY OF THE INVENTION

The swallow challenge medium of this invention has a number of advantages over traditional substances, e.g., water, saline solution, yogurt, mashed potatoes, and other foods, used for manometer and impedance testing of esophageal motility functions. To be truly useful in a broad sense, impedance and manometer (pressure) test results for esophageal motility functions and diagnostics should be consistent, dependable, repeatable, and accurate, not only for effective testing on individual patients, but also so that reliable standards can be developed and so that individual swallow tests can be compared to such standards in a meaningful manner and with a meaningful results. The swallow challenge medium of this invention provides dependable, controllable, and consistent viscosity, conductivity and impedance, and non-stick, surface tension characteristics to meet these goals with a long enough shelf life to remain dependable, consistent, and reliable for most ordinary users and uses in esophageal testing. It is also ingestible, food-grade material that is not harmful to humans.

Generally, according to one aspect of the invention, a swallow challenge medium is provided, which has a viscosity of about 1,000 centipoise to about 100,000 centipoise at 30 rpm when tested using a Brookfield Viscometer, LVT model, with a number-4 spindle. The medium is preferably, but not necessarily, thixotropic, exhibiting a decrease in viscosity by, for example, about 20-fold or more, over a two-decade increase in the rotation velocity of the viscometer spindle. It provides impedance of about 300 to 500 ohms, thus has conductivity in the range of about 4.5 to 7.6 millisiemens/cm (mS/cm). The medium can also have a pH of about 3.5 to about 9.0. The challenge medium includes water, a thickening agent such as a polysaccharide in general and carrageenan in particular, and an ion donor such as sodium chloride. It also includes preservatives such as sodium benzoate. All ingredients are food-grade.

According to another aspect of the invention, the swallow challenge medium also has very high surface tension so that it has a high cohesion (attraction to like molecules) and low adhesion (attraction to unlike molecules), which makes it substantially non-sticking to the impedance sensor electrode and probe surfaces.

According to another aspect of the invention, a method of measuring the physiological functions of an organ includes the following steps: (1) introducing a predetermined quantity of a challenge medium into the organ, (2) selecting a plurality of pairs of locations along a path in the organ, (3) measuring the impedance between each pair of positions, and (4) determining the location of the challenge medium along the path as a function of time. The challenge medium can be the challenge medium described above. The method can also include determining the pressure at a plurality of locations along the path in the organ as a function of time and comparing the location of the challenge medium along the path with pressure along the path as a function of time. The method can also include repeating the above steps a plurality of times and comparing the results with a standard.

Additional objects, advantages, and novel features of the invention are set forth in part in the description that follows and others will become apparent to those skilled in the art upon examination of the following description and figures or may be learned by practicing the invention.

BRIEF DESCRIPTION OF THE DRAWINGS

The accompanying drawings, which are incorporated in and form a part of the specification, illustrate the preferred embodiments of the present invention, and together with the written description and claims, serve to explain the principles of the invention. In the drawings:

DETAILED DESCRIPTION OF THE PREFERRED EMBODIMENTS

Figure 1:
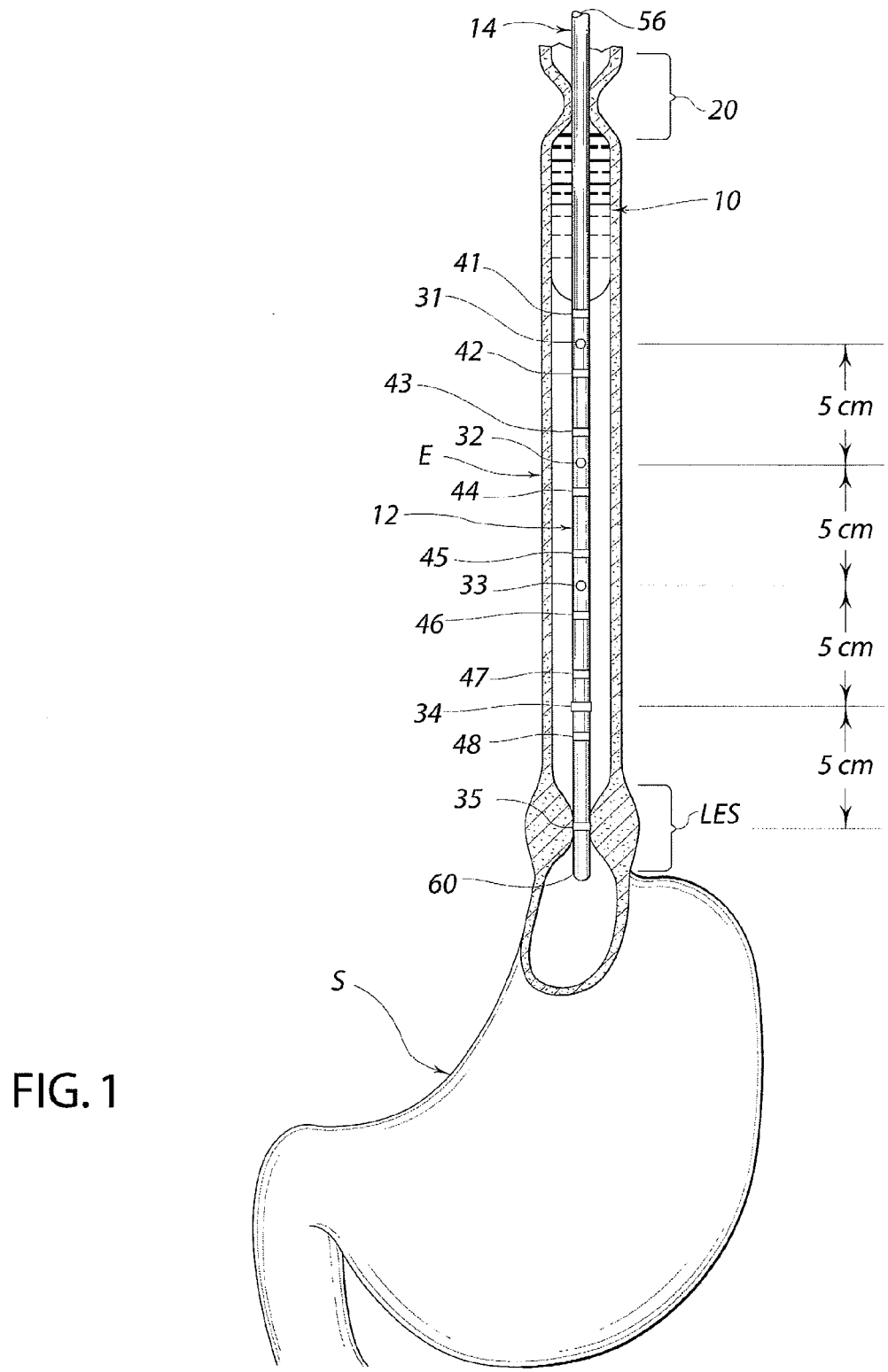
FIG. 1 is a diagrammatic illustration, in partially cross-sectioned elevation, of a swallow challenge medium used in conjunction with an impedance and manometric probe for assessing motility functions of a person's esophagus.

A swallow challenge medium 10 of this invention is illustrated diagrammatically in FIG. 1 positioned in a person's esophagus E along with a combination impedance and pressure measuring probe 12 on a catheter 14 for monitoring and/or testing motility function of the esophagus E and bolus transit dynamics through the esophagus E. Upon swallowing the swallow challenge medium 10, it forms a bolus in the person's esophagus E, and a normal esophageal function includes peristaltic muscular contractions 20 of the esophagus wall 16, as illustrated diagrammatically in FIG. 1, to propel the swallow challenge medium (bolus) 10 through the esophagus E to the person's stomach S. As will be explained in more detail below, the swallow challenge medium 10 provides a bolus that has optimal characteristics to enhance assessment of motility functions and malfunctions, including establishments of standards and comparison of individual cases to such standards.

One or more pressure sensors 31, 32, 33, 34, 35 and/or a plurality of impedance sensors 41, 42, 43, 44, 45, 46, 47, 48 on the probe 12 are used to detect and quantify peristalsis and bolus transit dynamics. The pressure sensors, in general, are more suited for use primarily to detect and quantify peristalsis, and the impedance sensors, in general, are more suited for use primarily to detect and quantify bolus transit dynamics, as will be discussed in more detail below. Therefore, while the most advantageous use of the swallow challenge medium 10 of this invention is with a probe that has both manometer (pressure) and impedance sensing functions, it can, of course, also be used with either a manometer or impedance sensor, separately.

The catheter 14 and probe 12, themselves, are not part of this invention, other than as they are used in combination with the swallow challenge medium 10 according to this invention. Manometer probes for such esophageal peristalsis measurements are well-known in the art and are available from a number of manufacturers. The impedance measuring features are described in U.S. Pat. No. 5,109,870, issued to Silny et al., which is incorporated herein by reference. A combination manometer and impedance catheter and probe is available from Sandhill Scientific, Inc., Highlands Ranch, Colo. Therefore, the pressure and impedance measuring capabilities of the probe 12 are described herein only to the extent necessary to explain the salient characteristics of the swallow challenge medium 10 and how it can be used according to this invention. Suffice it to say, therefore, that the example probe 12 illustrated in FIG. 1 is shown with a plurality of individual pressure sensors 31, 32, 33, 34, 35 interspersed with a plurality of impedance sensor contacts 41, 42, 43, 44, 45, 46, 47, 48 along a length of the probe section 12 of the catheter 14. The pressure sensors 31, 32, 33, 34, 35 are preferably spaced at known distances apart from each other to facilitate correlation of pressures sensed by the sensors 31, 32, 33, 34, 35 to specific physical locations in the person's esophagus. For example, if the pressure sensors 31, 32, 33, 34, 35 are spaced 5 cm apart along the length of the probe 12, and if the last pressure sensor 35 is positioned in the LES as illustrated in FIG. 1, then it can be assumed that pressure measurements from the sensors 31, 32, 33, 34 are indicative of pressures in the esophagus E at 20 cm, 15 cm, 10 cm, and 5 cm, respectively, above the LES. The probe 12 can be positioned in the esophagus E by inserting its distal end 60 and last pressure sensor 35 all the way into the stomach S and then pulling it back upwardly until the pressure sensor 35 detects the increased pressure that results from the pressure sensor 35 being positioned in the lower esophageal sphincter (LES). Of course, other spatial increments or distances can also be used, and more or fewer pressure sensors can be used, if desired. The pressure sensors 31, 32, 33, 34, 35 are connected to appropriate instrumentation, monitor, and display equipment (not shown in FIG. 1), which is also available from manufacturers or suppliers of the probes 12 or from other sources known to persons skilled in the art, thus do not need to be described here for an understanding of this invention.

Figure 2:
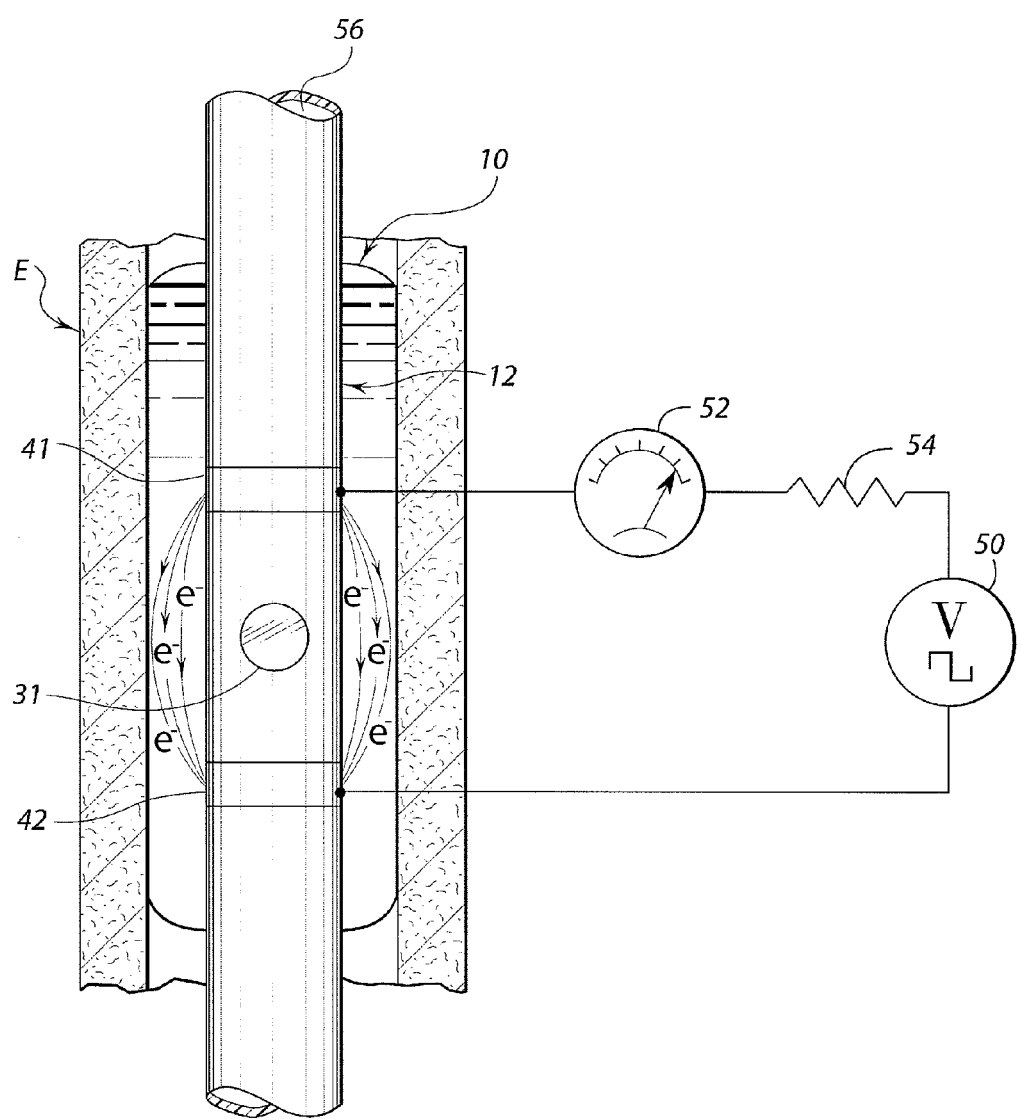
FIG. 2 is an enlarged view of the swallow challenge medium in the esophagus adjacent a pair of electric contacts on the probe in combination with a schematic diagram of simple impedance measuring circuit.

The impedance measurements are facilitated by the plurality of electrically conductive contacts or sensors 41, 42, 43, 44, 45, 46, 47, 48 dispersed spatially along the probe 12. Impedance, which is opposition to flow of electric current, can be measured between any of the contacts or sensors 41, 42, 43, 44, 45, 46, 47, 48, as illustrated diagrammatically in FIG. 2. While any impedance measuring instrumentation will work, the simple schematic circuit diagram in FIG. 2 illustrates the principle. A constant voltage source 50 is connected across a pair of the conductive contacts, e.g., contacts or sensor elements 41, 42, to make an electric current "e$^-$" flows between the contacts or sensor elements 41, 42. The current flow can be measured by an ammeter or similar instrumentation 52. According to Ohm's law, the magnitude of the electric current measured at 52 is proportional to the impedance of the material through which the electric current "e$^-$" flows between the contact or sensor elements 41, 42. Therefore, if the swallow challenge medium 10 of this invention is positioned across the contact or sensor elements 41, 42 of the probe 12, as illustrated in FIG. 2, the electric current measured at 52 is dependant at least in part on the impedance of the swallow challenge medium 10. On the other hand, if the swallow challenge medium 10 is not positioned across the two contacts 41, 42, then the current measurement at 52 will be inversely proportional to the impedance of whatever other material through which the current has to flow to complete the electric circuit, such as air, esophageal wall tissue, saliva, or whatever. The lower the impedance of the material across the contacts 41, 42, the greater the current flow will be, and vice versa. Some current control or limiting device or circuitry 54, represented generically as a resistor in FIG. 2, can be used to prevent the flow of too much electric current, which could burn or otherwise injure the tissue. Of course, the FIG. 2 is only schematic, and the actual wires or conductors used to connect the impedance sensors 41, 42, 43, 44, 45, 46, 47, 48 as well as the pressure sensors 31, 32, 33, 34, 35 to the instrumentation is routed through the lumen 56 in the probe 12 and catheter 14 to the exterior of the person's body.

Figure 3:
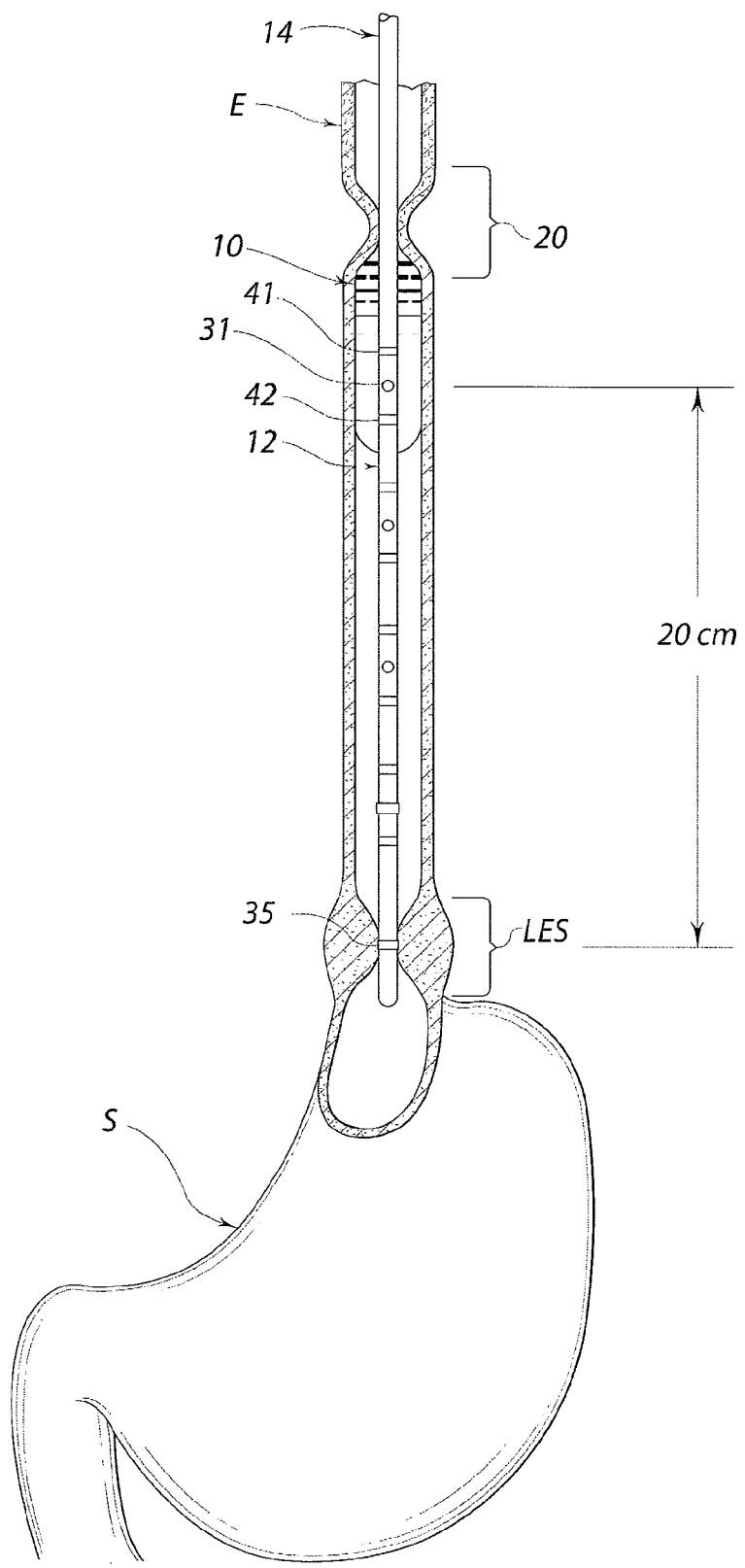
FIG. 3 is a view similar to FIG. 1, but showing a bolus of the swallow challenge medium moved into position adjacent a first pair of impedance sensor electrodes and a pressure sensor on the probe.

As mentioned above, the primary function of the pressure sensors 31, 32, 33, 34, 35 is to detect and monitor the peristaltic muscle contraction 20 as it progresses down the esophagus E, ideally to propel the swallow challenge medium 20 through the esophagus E to the stomach (FIG. 1), and the primary function of the impedance sensors 41, 42, 43, 44, 45, 46, 47, 48 is to detect and monitor transit of the bolus comprising the swallow challenge medium through the esophagus E to the stomach S. To illustrate, reference is made first to FIG. 1, in which the focus of swallow challenge medium 10 is shown positioned in the esophagus E above the first pressure sensor 31 and above the first impedance sensor pair 41, 42, where it is being propelled toward the stomach by the peristaltic muscle contraction 20. The LES is shown in FIG. 1 contracted around the probe 12, where the pressure sensor 35 is positioned near the distal end 60, as explained above. Both the pressure measurements and the impedance measurements are just background or base levels at this point, because both the swallow challenge medium 10 and the peristaltic muscle contraction 20 are still above the pressure sensors 31, 32, 33, 34, 35 and the impedance sensors 41, 42, 43, 44, 45, 46, 47, 48 of the probe 12. Referring now to FIG. 3, where the peristaltic muscle contraction 20 has propelled the swallow challenge medium 10 to a position surrounding the first pair of impedance sensor contacts 41, 42, and the first pressure sensor 31. Since the swallow challenge medium 10 is formulated to have a low impedance, as will be discussed in more detail below, the flow of electric current e⁻(FIG. 2) increases as soon as both sensors 41, 42 are contacted by the swallow challenge medium 10. Therefore, a decrease in impedance across the sensor contacts 41, 42 detected by the impedance detector instrumentation 52 indicates the arrival of the swallow challenge medium 10 at the location of the impedance sensor pair 41, 42. Meanwhile, as shown in FIG. 3, the peristaltic muscle contraction 20, which follows the swallow challenge medium bolus 10, has not yet reached the location of the first pressure sensor 31, which in the example described above, is about 20 cm above the LES. Therefore, while a decrease of impedance across the first pair of sensor contacts 41, 42 indicates the swallow challenge medium 10 has arrived at the location about 20 cm above the LES, the lack of any simultaneous increase of pressure at the first pressure sensor 31 indicates that the peristaltic muscle contraction has not yet arrived at the location 20 cm above the LES. When the contraction 20 does arrive at that position, it will apply its contraction pressure on the pressure sensor 31. Therefore, a pressure increase detected by pressure sensor 31 will indicate that the contraction 20 has arrived at that location.

Figure 4:
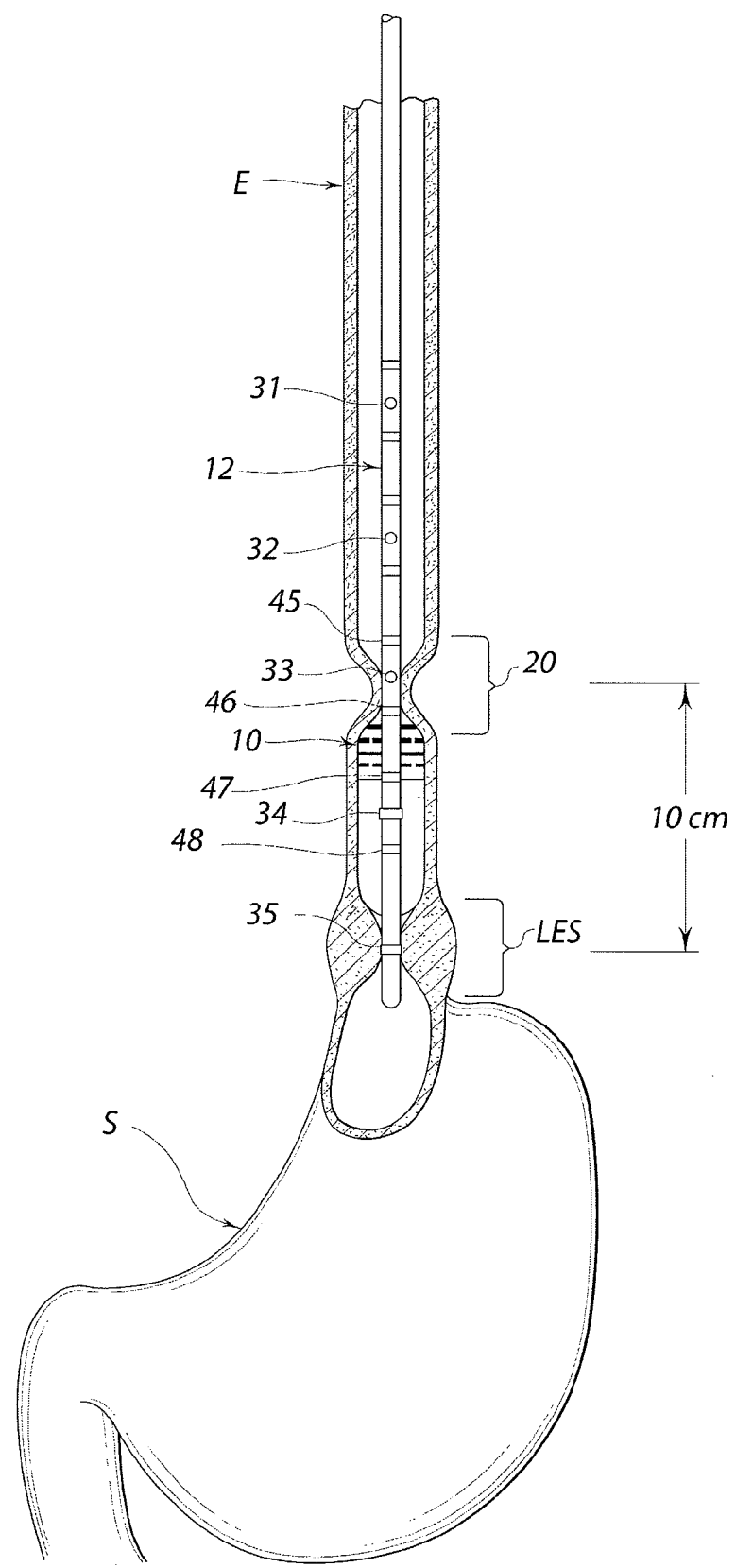
FIG. 4 is a view similar to FIGS. 1 and 3, but with the swallow challenge medium bolus moved to a position immediately above the lower esophageal sphincter (LES)

Next the illustration in FIG. 4 shows that the peristaltic muscle contraction 20 has progressed past the first and second pressure sensors 31, 32 to a position at or slightly below the third pressure sensor 33, where it has pushed the swallow challenge medium bolus 10 to a position just above the LES. This position of the swallow challenge medium 10 is detected by the last pair of impedance sensor contacts 47, 48 and possibly by impedance sensor contacts 46, 47, both of which are also still in contact with the swallow challenge medium 10 in this position. Also, the movement of the peristaltic muscle contraction 20 to this position is, or just was, detected by the third pressure sensor 33.

Figure 5:
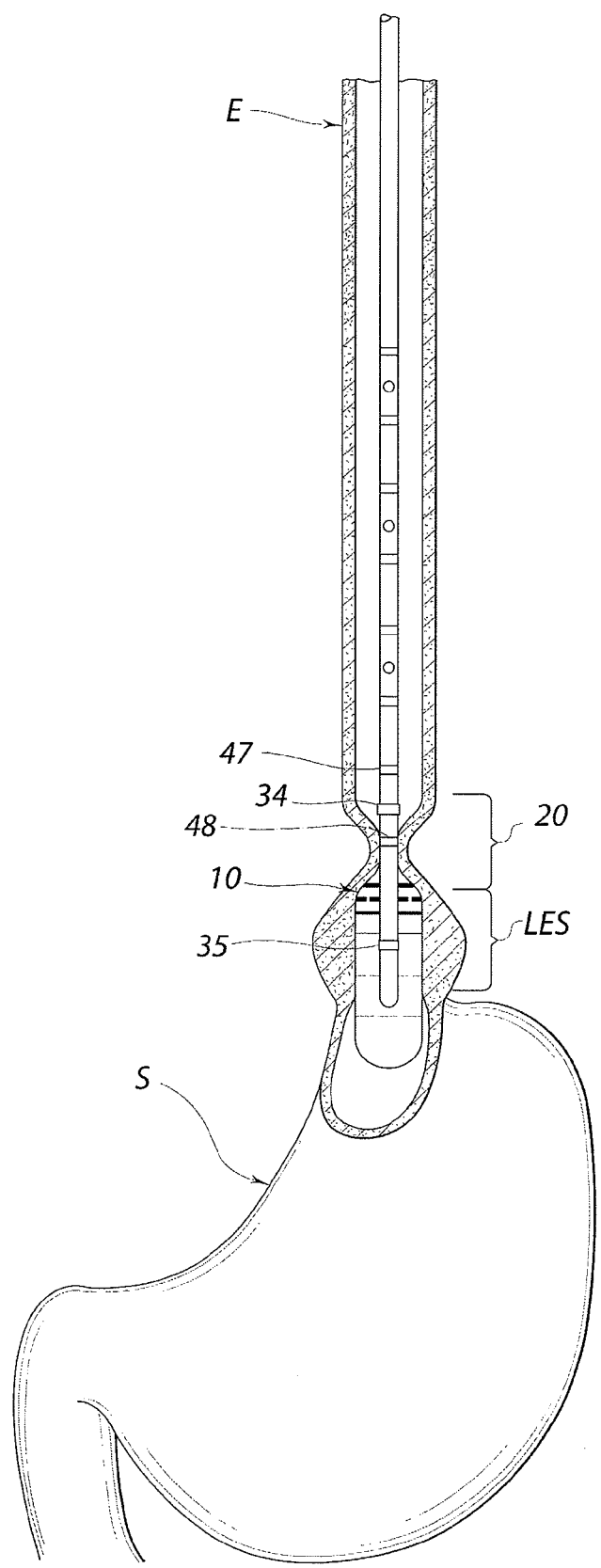
FIG. 5 is a view similar to FIGS. 1, 3, and 4, but with the swallow challenge medium bolus moving through the LES from the esophagus into the stomach.

Finally, as illustrated in FIG. 5, as the peristaltic muscle contraction 20 continues to propel the swallow challenge medium 10 toward the stomach S, the passing of the contraction 20 would have been detected by the fourth pressure sensor 34, and the LES opens momentarily for the swallow challenge medium bolus 10 to enter the stomach S.

Figure 6:
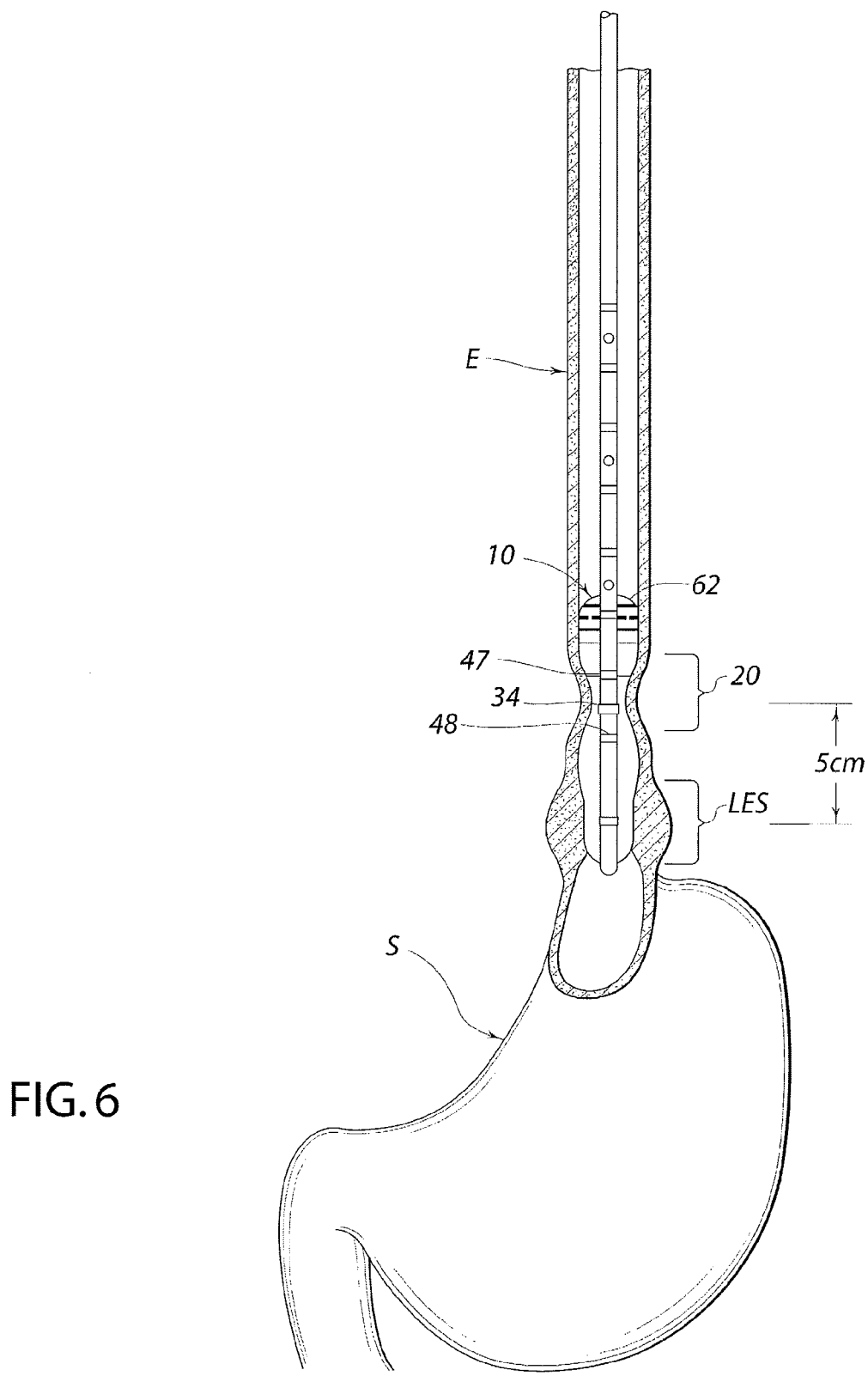
FIG. 6 is a view similar to FIGS. 1 and 3–5, but illustrating an example of an unsuccessful swallow with the swallow challenge medium partially through the LES and partially behind the peristaltic muscle contraction in the esophagus.

All of the peristalsis and bolus transit functions described above are normal for a healthy esophagus E and LES. However, an important feature of this invention is to facilitate diagnosis of defective or malfunctioning peristalsis and bolus transit and/or LES malfunctions. One example of this capability is illustrated in FIG. 6, wherein the swallow challenge medium bolus 10 is not transmitted successfully through the LES and into the stomach S before the peristaltic muscle contraction reaches the bottom of the esophagus E and terminates that peristaltic cycle. As illustrated in FIG. 6, there is a condition of bolus stasis in which a portion of the swallow challenge medium bolus 10 is still above the LES as the peristaltic contraction 20 by-passes at least the upper portion 62 portion of the bolus 10 instead of pushing it through the LES and into the stomach S. Therefore, the bolus transit is incomplete. This incomplete bolus transit is detectable by the impedance measurements between sensor contacts 47, 48 and/or sensor contacts 46, 47 still showing the presence of the swallow challenge medium 10 more than 5 cm above the LES, while the fourth pressure sensor 34 shows that the peristaltic muscle contraction 20 has already progressed to within 5 cm of the LES. In other words, this example condition indicates that the peristaltic muscle contraction 20 is not successfully propelling the bolus 10 through the LES and/or the LES is not admitting the bolus 10 into the stomach. This and other peristalsis and bolus transit problems can be detected more reliably and in a repeatable manner with the swallow challenge medium 10 of this invention than with the use of water, saline solution, or other bolus materials, as will be explained in more detail below.

Another example abnormal pattern (not illustrated), which can be detected is retrograde bolus movement in which the swallow challenge medium or other bolus moves in a reverse direction, upwardly in the esophagus, after the peristaltic wave passes the bolus. Again, the pressure sensors 31–35 would show passage of the peristaltic wave down the esophagus, while the impedance sensors 41–48 would show the bolus moving in the opposite direction. These and other abnormal peristalsis and bolus transit patterns can indicate various disease states or conditions, as will be understood by persons skilled in this art.

Figure 7:
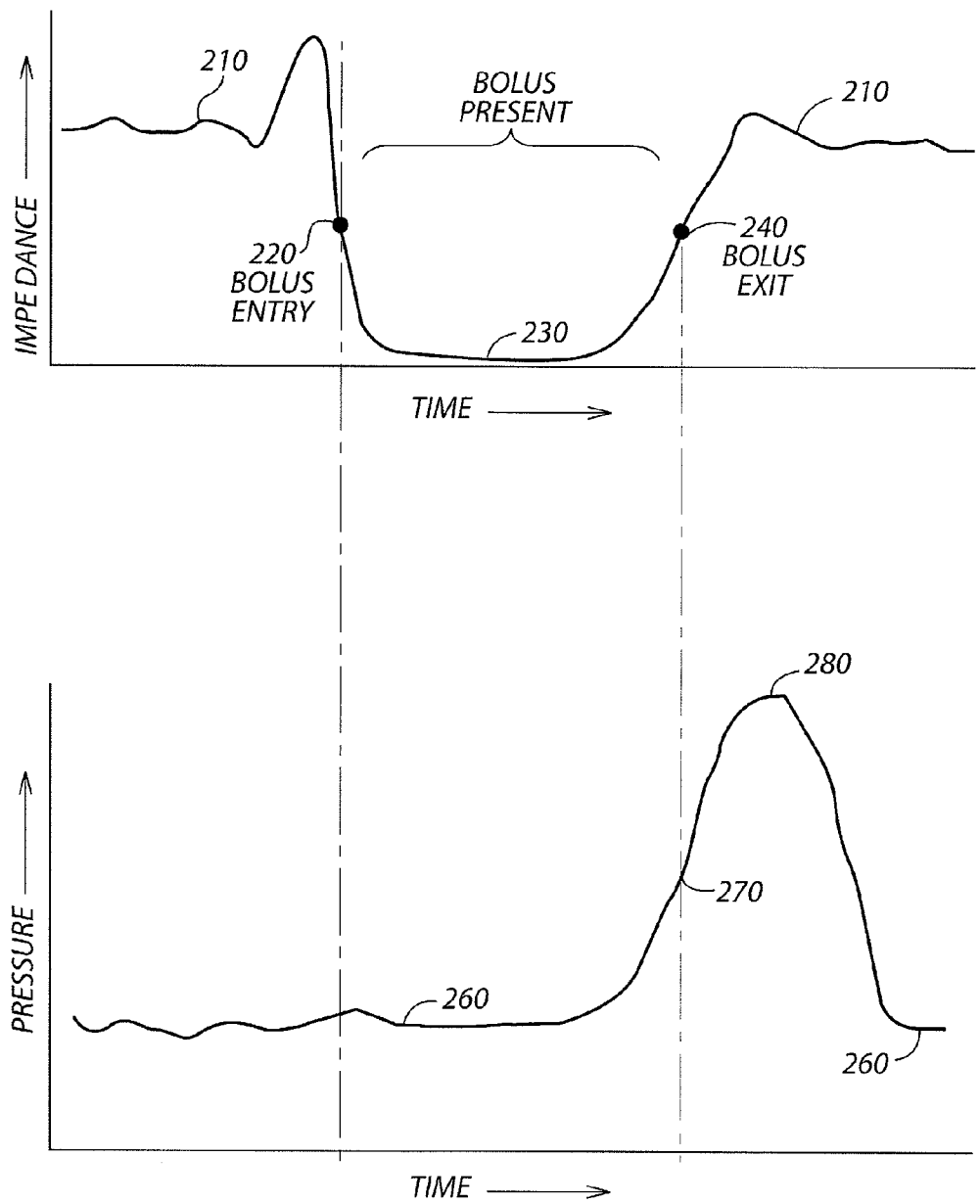
FIG. 7 is a graphical illustration of impedance/time and pressure/time profiles of a normal swallow in relation to a sensor location on a probe positioned in a person's esophagus.

Typical impedance and pressure measurement profiles at one location on the probe 12, for example, at the first impedance sensor contacts 41, 42 and the first pressure sensor 31 about 20 cm above the LES, are shown in FIG. 7 for normal peristalsis and bolus transit similar to that illustrated in FIGS. 1 and 2 and described above. Prior to the arrival of the swallow challenge medium bolus 10 at this location, the impedance meter 52 (FIG. 2) reads a background or base impedance 210 (FIG. 7) from the sensor contact pair 41, 42. The background or base impedance 210 is a function of the conductivity and mass of any esophageal wall tissues, air, or other fluids surrounding and between the electrodes 41, 42. Suitable manometer (pressure meter) instrumentation (not shown) reads the background or base pressure 260 (FIG. 7) during this initial time period.

The person is then instructed to swallow a predetermined amount, for example 5 ml, of the swallow challenge medium 10, which has an electrical conductivity that is higher than that of the esophageal tissues and other materials that provide the background or base impedance 210 discussed above. A particularly advantageous type of swallow challenge medium 10 according to this invention is described in more detail below. As the bolus of the swallowed challenge medium 10 advances down the esophagus E and passes the first pair of electrodes 41, 42, the impedance between the electrodes begins to drop, as indicated at 220 in FIG. 7, approximately when the bolus 10 reaches the upper electrode, i.e., sensor contact 44. Once the bolus of swallow challenge medium 10 bridges the upper and lower electrodes 41, 42, as shown in FIG. 2, the impedance 230 (FIG. 7) remains substantially at the lowest level 230 until the tail end of the bolus 10 moves beyond the upper electrode 41. The impedance then begins to increase, as indicated at 240 (FIG.

7) until the bolus 10 is completely detached from both electrodes 41, 42, whereupon the impedance returns to the background level 210.

In the meantime, for the pressure sensor 31 located midpoint between the two electrodes 41, 42 that give rise to the impedance curve in FIG. 7 described above, the background pressure 260 for normal peristalsis prior to and during the time period when the bolus 10 comes into contact with the electrodes 41, 42, because the muscular contraction 20 (FIG. 2) of the esophagus E propelling the bolus 10 is still upstream from the first pressure sensor 31. However, when the muscle contraction 20 passes the first electrode 41 and approaches the pressure sensor 31, the pressure at the pressure sensor 31 begins to rise, as indicated at 270 in FIG. 7, at about the same time as the rising impedance 240 indicates the bolus 10 is moving away from that location on the probe 12. The pressure reaches its peak 280, when the muscle contraction 20 is at the sensor 31 and then returns to the background pressure 260 as the muscle contraction 20 passes beyond the first pressure sensor 31.

Thus, the time profiles of both impedance and pressure, as well as the timing relationship between the two profiles illustrated in FIG. 7 can be used to detect abnormalities of the esophageal motility function. For example, if the impedance at a particular pair, such as electrodes 41, 42, should ever remain at or near the minimum value 230 and not return to the background level for a prolonged period of time (such as beyond the time when a pressure peak 280 is detected at that location or when such a pressure peak 280 is detected by a subsequent pressure sensor 32, 33, or 34 downstream this scenario could be an indication that the peristalsis was ineffective in propelling the bolus 10 past the electrodes 41, 42.

Figure 8:
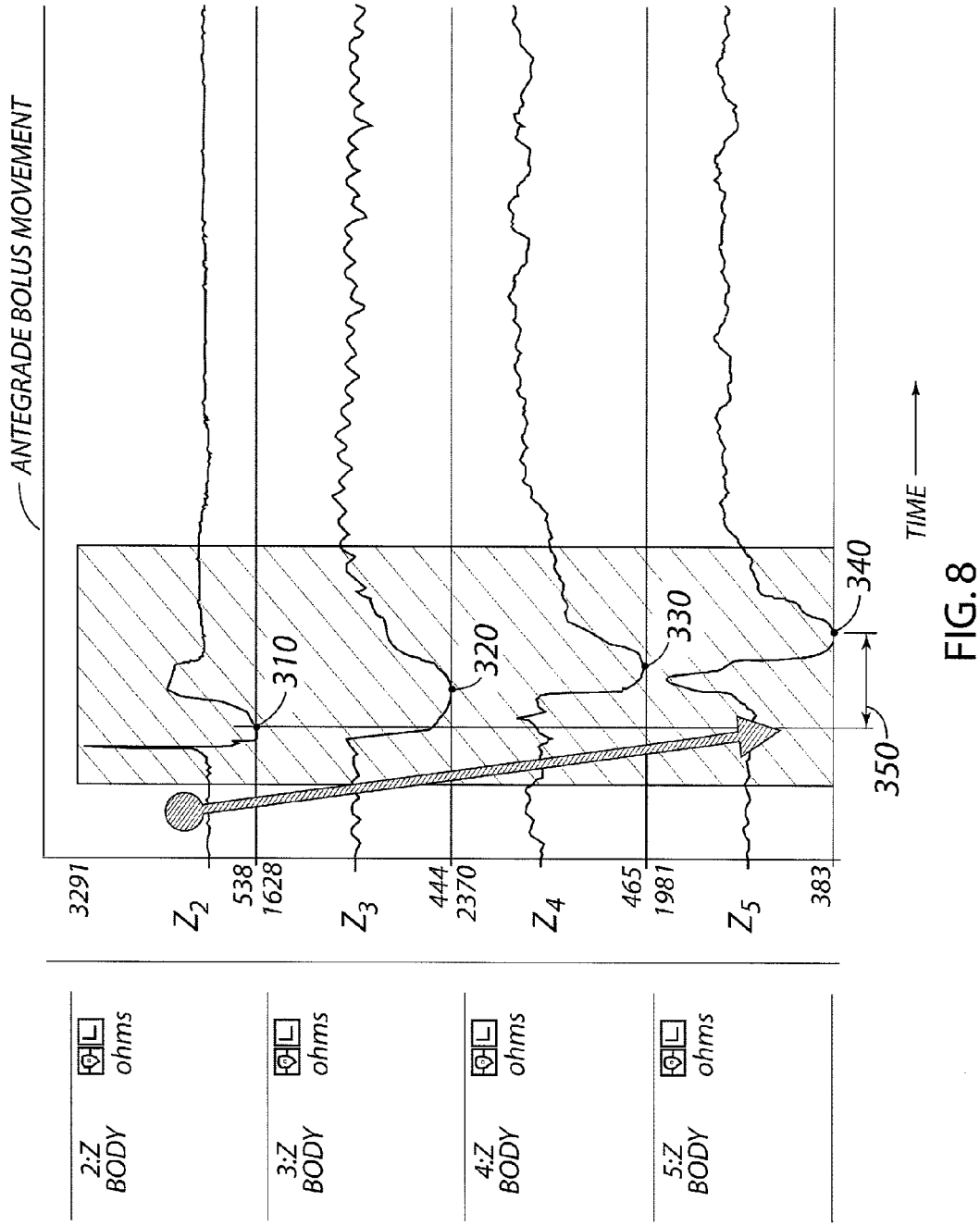
FIG. 8 is an example of a 4-channel impedance/time profile of a swallow to illustrate functions of this invention.

As discussed above, the timing of the pressure peaks 280 detected at the pressure sensors 31, 32, 33, 34 along the esophagus E can be used to measure the velocity of peristaltic propagation of the esophageal muscular contraction 20. Similarly, the timing of the impedance troughs 230 detected at successive electrode pairs 41–42, 42–43, 43–44, 44–45, 45–46, 46–47, 47–48 (or fewer of these pairs) can be used to measure the velocity of bolus transit. For example, a set of four impedance/time profiles measured on four impedance channels of a probe 12 derived from four electrode pairs 41–42, 43–44, 45–46, 47–48, respectively, in a swallow test is shown in FIG. 8. In this example, the pairs of electrodes are spaced apart at a center-to-center distance of 5 cm. The electrode pairs are numbered 2, 3, 4 and 5, respectively, from the uppermost pair 41–42 to the lowermost pair 47–48. The impedance values are labeled, respectively, $Z_2$, $Z_3$, $Z_4$, and $Z_5$. As seen in FIG. 8, the impedance trough 310 appears in $Z_2$ first and progressively later in $Z_3$ (320), $Z_4$ (330) and $Z_5$ (340). The time interval 350 between the troughs 310, 340 $Z_5$ and $Z_2$, i.e., for the bolus 10 to travel the 15 cm from the first electrode pair 41–42 and the last electrode pair 47–48, is about five seconds, corresponding to a bolus transit velocity of about 3 cm/s.

The patient can be instructed to perform a predetermined number (such as ten) of swallows of the swallow challenge medium 10, with the swallows spaced apart by a predetermined amount of time (such as about 30 seconds). A statistical analysis can then be performed on the data, and the result compared to a standard to determine whether the esophageal functions of the esophagus E are within or outside normal parameters. For example, if a physician finds that five out of ten swallows by a patent fail to achieve complete transit of the swallow challenge medium bolus 10 to the stomach S, when the standard for a healthy esophagus is no more than three out of ten failed bolus transits for the type of the particular swallow challenge medium used, that particular patient's failure rate may indicate esophageal motility abnormalities. From the location of the electrode pair that produced the abnormal impedance profile, especially if viewed in relation to the progression of the peristaltic muscle contractions 20 as monitored by the pressure sensors 31, 32, 33, 34, 35 as explained above, the approximate location of a suspect region in the esophagus can also be determined. As another example, the bolus transit velocities can also be compared to a standard to assess the condition of the esophagus.

However, comparing the results of the impedance measurements and/or pressure measurements with a standard is only meaningful, where not only the test conditions, materials, and equipment are standard, but also where they are designed to bring out or induce a manifestation of abnormalities that may exist. Test swallows performed with higher viscosity materials provide greater sensitivity to the detection and quantification of abnormal esophageal motility or diseased states.

As described in more detail below, the invention provides a viscous swallow challenge medium 10 with characteristics that satisfy this requirement as well as other desirable features for use in such swallow tests for esophageal motility evaluations and diagnostics.

The swallow challenge medium 10 of this invention is substantially more viscous than water in order to provide a more vigorous swallow test, but which can still be swallowed without the aid of a liquid by a person with a healthy esophagus. More viscosity also provides a more tightly contained bolus (short length) that keeps the impedance measurements of the swallow challenge medium 10 more tightly confined to fewer of the impedance sensor electrodes 41–48, thus providing more concise bolus location data at any instant in time. Also, at tighter bolus 10, due to its higher viscosity as well as its higher surface tension, also advances only in response to the propulsive force of the peristaltic muscle contractions. In contrast, water, for example, flows by gravity and fills the entire length of the esophagus, which obscures impedance location data and does not challenge the peristaltic muscle contractions in the esophagus. For example, the swallow challenge medium 10 can have a viscosity of about 1,000 to about 100,000 centipoise at 30 rpm (i.e., high shear test) using a Brookfield Viscometer, LVT model, with a number-4 spindle, preferably from about 5,000 to about 50,000 centipoise, and more preferably from about 6,000 to about 20,000 centipoise for comfortable swallows and at least minimally effective impedance measuring of bolus transit dynamics. It is also preferred that the viscosity not vary substantially in the shelf life of the swallow challenge medium 10, preferably not more than about 15%.

For such viscosity shelf life stability, especially for polysaccharide thickening agents, the pH of the swallow challenge medium 10 should be in the range of 3.5 to 9.0, preferably about 4.0 to 9.0, and more preferably 4.5 to 8.0. The desired viscosity is largely achieved and controllable by including a proper amount of thickening agent and liquid, such as water, in the ingredients. A number of known food-grade thickening agents can be used, including polysaccharides, such as carrageenan, jells, or hydrojells.

It is also preferred, although not essential, that the swallow challenge medium not only be viscous, but that it also be thixotropic, i.e., that it has a variable viscosity such that it acts more like a solid (higher viscosity) at low shear and more like a liquid (lower viscosity) at high shear. As mentioned above, a more viscous swallow challenge medium 10 provides a more rigorous swallow test that is more likely to induce manifestation of abnormalities in esophageal motility in fewer swallow tests than, for example, water or saline solution. Also, test swallows using water may result in a patient showing a 20% rate of ineffective swallow peristalsis, whereas testing the same patient with a viscous swallow challenge medium, e.g., about 90,000 centipoise, may show a higher rate of swallow failures, such as 40%. In addition, abnormalities in esophageal motility may be more pronounced in slower bolus transit velocity with a more viscous swallow challenge medium 10 than with water or saline solution, at least in part because a more viscous swallow challenge medium 10 has to be propelled through the esophagus by the peristaltic muscle contractions 20 (FIGS. 1 and 2–6), whereas water may simply gravity flow at a high velocity through the esophagus regardless of the strength or effectiveness or velocity of the peristaltic muscle contractions in the esophagus. However, a constant high viscosity material may be difficult for a patient to swallow without gagging or psychological resistance to even getting it out of the mouth and into the esophagus. A thixotropic swallow challenge medium 10 alleviates this problem by feeling and flowing more like a low viscosity liquid in the initial swallow process, which is a higher shear condition, and then being more like a high viscosity liquid or solid, once it is in the esophagus where the shear conditions are lower.

Therefore, in addition to having the high shear viscosity characteristics described above, it is also desirable to have a higher viscosity in low shear conditions. Consequently, a low shear (0.3 rpm on the same Brookfield viscometer as that described above) viscosity swallow challenge medium in a range of about 50,000 to 800,000 equipoise is desirable, preferably about 100,000 to 600,000 equipoise, and more preferably about 300,000 to 500,0000 equipoise. Also, a medium shear (3.0 rpm on the same Brookfield viscometer as that described above) viscosity for the swallow challenge medium may be in a range of about 10,000 to 300,000 equipoise, preferably about 50,000 to 200,000 equipoise, and more preferably about 80,000 to 100,000 equipoise. A decrease in viscosity by, for example, about twenty-fold or more over a two-decade increase in the rotation velocity of the viscometer spindle is a good thixotropic characteristic.

The swallow challenge medium of this invention also preferably has a high electrical conductivity in contrast to a substantially lower conductivity of the tissue lining of the esophagus to enable accurate impedance measurements with equipment such as that described above and to enable a clear, highly detectable drop in impedance when the swallow challenge medium 10 moves into contact with the sensor electrodes 41–48. For example, the swallow challenge medium preferably has a conductivity of about 4.5 mS/cm to about 7.6 mS/cm. These electrical conductivities can be achieved by a sufficiently high ionic density in the swallow challenge medium 10, and such high ionic density can be achieved and controlled by including a proper amount of any food grade ion donors, such as sodium chloride. The ionic density can be controlled at a sufficiently high level so that a relatively small amount, such as 5 ml, of the swallow challenging medium 10 produces adequate amount of change in impedance between a pair of electrodes 41–42, 42–43, 43–44, 44–45, 45–46, 46–47, 47–48 (FIGS. 1 and 2–6) when the swallow challenge medium bolus 10 bridges the electrodes to provide a clear reading or indication of real time swallow challenge medium bolus 10 position in the esophagus by the impedance detector circuits, as described above. With sufficient ionic content to get the conductivity of the swallow challenge medium into the preferred 4.5 to 7.6 mS/cm range mentioned above, as little as 1 ml. of the swallow challenge medium can be detected with a probe that has impedance sensor electrodes 41–48 spaced as shown in FIG. 1, i.e., approximately 2.5 cm apart.

As mentioned above, it is also preferred that the swallow challenge medium has a very high surface tension so that it does not coat and cling to the surfaces of the electrodes 41–48 and/or probe 12 with enough residue to introduce a significant amount of error in the subsequent impedance measurements. In other words, it is desirable to not only have a clear reading of the low impedance presence of the swallow challenge medium bolus 10, when it is present at a particular electrode or contact pair location, as explained above, but it is also desirable to have a clear higher impedance reading from those same electrode or contact pairs when the swallow challenge medium bolus 10 passes that location. Otherwise, not only will the impedance readings from those electrodes not return to base impedance level and indicate when the bolus 10 has moved past those electrodes, they may also not be able to indicate when swallow challenge media from subsequent swallows arrive at those electrodes. Therefore, it is important to not have the swallow challenge medium 10 that leaves a coating or enough residue on the surfaces of the electrodes 41–48 and probe 12 to bridge pairs of electrodes and carry electric current between them after the bolus of swallow challenge medium has passed. As mentioned above, a high surface tension in the swallow challenge medium solves this problem. High surface tension is characterized by high cohesive strength, i.e., attraction to like molecules, and low adhesion, i.e., low or negligible attraction to unlike molecules. Surface tension of a material in relation to material-to-electrode surface and material-to-probe surface, instead of conventional material-to-air surface tension parameters, is difficult to quantify directly. However, in this application, the non-coating property can be quantified indirectly by comparing impedance measured across a pair of electrodes before contact with the swallow challenge medium with impedance measured across the pair of electrodes after contact with the swallow challenge medium. For example, it can be done by first measuring the impedance between a pair of the electrodes or contacts, e.g., electrodes 41–42, on the probe 12 in dry air. Second, immerse the probe 12 and electrodes 41–42 in a sample of the swallow challenge medium and pull it out of the medium. Third, without wiping the probe 12 or electrodes 41–42, measuring the impedance again across the electrodes 41–42. If the second impedance measurement after immersion and withdrawal of the electrodes from the swallow challenge medium samples is substantially the same as the impedance reading before the immersion, the indication is that very little, if any, of the swallow challenge medium sample remained on the probe 12 and electrodes 41–42, thus did not stick. For example, a drop of 20% or less in impedance in this kind of test may be considered an indication of an adequate non-stick characteristic, although a drop of 10% or less is preferred, and a drop of 1% or less is even more preferred.

Healthy esophageal tissue lining has an impedance of about 1,000 to 3,000 ohms. Therefore, the swallow challenge medium should at least have an impedance of about 300 to 600 ohms, when it is diluted with saliva, which may be slightly higher than the impedance of the swallow challenge medium itself before it is diluted with saliva from the mouth and esophagus.

For palatability, sweeteners such as sugar or sucralose, and flavoring agents, such as artificial banana, cherry, grape or pineapple flavors can be included in the swallow challenge medium. Preservatives and mold and yeast inhibitors can also be included to ensure adequate shelf life, for example a year or more. Another attribute of the swallow challenge medium is its non-allergenic property. All ingredients are food-grade. Particularly useful for diabetic patients is the variety in which sugar is replaced with an artificial sweetener, such as sucralose.

An example, a swallow challenge medium can be made by first blending the following ingredients together:

| | |
|---|---|
| Gelcarin GP 539 | 1.9 g |
| Potassium citrate monohydrate | 0.24 g |
| Sodium chloride | 0.16 g |
| Sodium benzoate | 0.15 g |
| Potassium sorbate | 0.15 g |
| Sucralose | 0.02 g |
| Yellow #5 | 0.001 g |

140 g of de-ionized water is then added to the blend with vigorous mixing. The resultant slurry is heated to about 50–100° C., preferably about 70° C., to dissolve the solids. While the solution is stirring, 0.38 g of banana flavor and 0.22 g citric acid can be dissolved in 7 g of de-ionized water to form an acidified flavoring solution. The heated solution can then be removed from the heat, and the acidified flavoring solution can be added with stirring to disperse it evenly. The mixture can then be decanted into a suitable vessel and cooled before using.

A swallow challenge medium prepared in this manner was tested for various properties. For viscosity measurement, a Brookfield Viscometer, LVT model, with a number-4 spindle was used at three different levels of shear (spindle velocities). The conductivity and impedance were determined by measuring electric current between a pair of electrodes 5 cm from each other and submerged in a cylinder of the swallow challenge medium 2 cm in diameter. The pH was also measured. The results are listed in Table I.

TABLE I

| Property | Value |
|---|---|
| Viscosity (centipoises) | 460,000 at spindle velocity 0.3 rpm |
| | 90,000 at spindle velocity 3.0 rpm |
| | 13,500 at spindle velocity 30 rpm |
| Conductivity (mS/cm) | 5.7 |
| Impedance (Ohms) | 400 |
| pH | 4.5 |

While a workable swallow challenge medium for some aspects of this invention can be within the ranges described above, one aspect of this invention is to provide a swallow challenge medium that has sufficiently consistent physical properties to be useable as a reliable standard swallow challenge medium, for compilation of reliable and meaningful standards for healthy esophageal motility functions, and for meaningful comparisons of individual esophageal test results to such standards. For such a standardizable quality, it is desirable to keep the physical properties of the swallow challenge medium within 15% of those values shown in Table I above, i.e., low shear (Brookfield 0.3 rpm) viscosity of 391,000 to 529,000 centipoises, medium shear (Brookfield 3.0 rpm) viscosity of 76,500 to 103,500 centipoises, high shear (Brookfield 30 rpm) viscosity of 11,475 to 15,525 centipoises, conductivity of 4.8 to 6.6 mS/cm, impedance of 340 to 460 ohms, and/or pH of 3.8 to 5.2. These viscosity measurements are based on the same Brookfield parameters and equipment as described above.

A prototype and three additional samples were also prepared with substantially the same recipe as above, but with sugar rather than sucralose. The characteristics are listed in Table II.

TABLE II

| Sample | Low Shear (Spindle Velocity = 0.3 RPM) | Medium Shear (Spindle Velocity = 3.0 RPM) | High Shear (Spindle Velocity = 30 RPM) |
|---|---|---|---|
| Prototype | 420,000 | 98,000 | 16,000 |
| 1 | 400,000 | 90,000 | 13,000 |
| 2 | 420,000 | 86,000 | 12,000 |
| 3 | 420,000 | 86,000 | 11,000 |

The conductivity of the three samples were, respectively, 4.14, 4.15 and 4.22 mS/cm. The pH values were, respectively, 4.58, 4.60 and 4.60.

The non-sticking property of a swallow challenge medium prepared in a manner similar to those used in the examples above was measured by measuring the impedance between a pair of electrodes on a probe (Sandhill Scientific, Inc., model MII) before and after the electrodes were immersed four inches deep in the sample swallow challenge medium in a tube of 2.0 cm in diameter without cleaning the probe after removal. The impedance was 11,800 ohms before immersion, 450 ohms during immersion, and 11,600 ohms after removal, i.e., a decrease in impedance of only 0.2% from pre-immersion to post-removal.

It should be noted that the choice of one or more ingredients for one property may affect one or more other properties of the challenge medium. Thus, to produce a challenge medium with a different combination of desired properties or to substitute one or more ingredients to obtain a challenge medium with the same set of properties may require multiple iterations of adjustment of ratios of ingredients. Such adjustments, however, are within the competence of persons skilled in the art such that he/she will be able to achieve the desired alternative properties and/or ingredients without undue experimentation. Also, while the description above is made with primary references and illustrations relating to the esophagus and esophageal peristalsis and bolus transit dynamics, it is also applicable to the oropharynx and diagnostics of swallow disorders in the oropharynx. Therefore, rather than repeat everything described and claimed herein for the oropharynx and oropharyngeal bolus transit dynamics the descriptions, references, and claims of this invention in relation to the esophagus are considered to also include the oropharynx muscular movements and oropharygeal bolus transits during swallowing.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

The foregoing description is considered as illustrative of the principles of the invention. Furthermore, since numerous modifications and changes will readily occur to those skilled in the art, it is not desired to limit the invention to the exact construction and process shown and described above. Accordingly, resort may be made to all suitable modifications and equivalents that fall within the scope of the invention. The words "comprise," "comprises," "comprising," "include," "including," and "includes" when used in this specification are intended to specify the presence of stated features, integers, components, or steps, but they do not preclude the presence or addition of one or more other features, integers, components, steps, or groups thereof.

The embodiments of the invention in which an exclusive property or privilege is claimed are defined as follows:

1. A method of testing peristalsis and bolus transit in a person's esophagus comprising:
   positioning a probe comprising a plurality of electrodes in longitudinally spaced relation to each other in the person's esophagus;
   having the person swallow a swallow challenge medium that has viscosity in a range of 1,000 to 100,000 centipoise (high shear), conductivity in the range of 3.8 to 7.6 mS/cm, and sufficient surface tension to cause the swallow challenge medium to clear sufficiently from surfaces of the electrodes and probe as the swallow challenge medium passes the electrodes and probe such that impedance measurements across the electrodes after the swallow challenge medium passes the electrodes is not less than 50% of impedance measurements across the electrodes before the challenge medium reaches the electrodes;
   measuring impedance across the electrodes on a real time basis as the challenge medium moves though the esophagus, and
   recording the impedance measurements as a function of time.

2. The method of claim 1, wherein the surface tension is sufficient such that said drop in impedance is not more than 1%.

3. The method of claim 1, wherein the swallow challenge medium is thixotropic.

4. The method of claim 1, wherein the swallow challenge medium has conductivity in a range of 4.5 to 7.6 mS/cm.

5. The method of claim 1, wherein the swallow challenge medium provides impedance in a range of 300 to 600 ohms.

6. The method of claim 1, wherein the swallow challenge medium provides impedance in a range of 300 to 500 ohms.

7. The method of claim 1, wherein the swallow challenge medium has pH in a range of 3.5 to 9.0.

* * * * *